United States Patent
Scheibengraber et al.

(10) Patent No.: US 8,077,328 B2
(45) Date of Patent: Dec. 13, 2011

(54) VARIABLE COLOR INCOHERENT ALIGNMENT LINE AND CROSS-HAIR GENERATOR

(75) Inventors: Karl Scheibengraber, Sussex, WI (US); David Schmocker, Sullivan, WI (US); Kenneth Freeman, Stow, OH (US)

(73) Assignee: Gammex, Inc., Middleton, WI (US)

( * ) Notice: Subject to any disclaimer, the term of this patent is extended or adjusted under 35 U.S.C. 154(b) by 55 days.

(21) Appl. No.: 12/823,752

(22) Filed: Jun. 25, 2010

(65) Prior Publication Data
US 2011/0001987 A1 Jan. 6, 2011

Related U.S. Application Data (60) Provisional application No. 61/223,212, filed on Jul. 6, 2009.

(51) Int. Cl.
*G01B 11/14* (2006.01)
(52) U.S. Cl. ...................................................... 356/622
(58) Field of Classification Search .................. None
See application file for complete search history.

(56) References Cited

U.S. PATENT DOCUMENTS

| | | | |
|---|---|---|---|
| 3,818,222 A * | 6/1974 | Jensen et al. ............ 250/214 LA |
| 4,117,337 A | 9/1978 | Staats |
| 4,223,227 A | 9/1980 | Horwitz |
| 4,242,587 A | 12/1980 | Lescrenier |
| 4,385,397 A | 5/1983 | Verro |
| 4,416,022 A | 11/1983 | Cutter |
| 4,426,726 A | 1/1984 | Cheetham |
| 4,538,289 A | 8/1985 | Scheibengraber |
| 4,618,980 A | 10/1986 | Lescrenier et al. |
| 4,693,567 A | 9/1987 | Ozaki |
| 4,730,895 A | 3/1988 | Siedband et al. |
| 4,752,948 A | 6/1988 | MacMahon |
| 4,836,671 A | 6/1989 | Bautista |
| 4,896,343 A | 1/1990 | Saunders |
| 5,038,260 A | 8/1991 | Scheibengraber |
| 5,095,386 A | 3/1992 | Scheibengraber |
| 5,320,111 A | 6/1994 | Livingston |
| 5,388,143 A | 2/1995 | MacMahon |
| 5,598,269 A | 1/1997 | Kitaevich et al. |
| 5,657,368 A | 8/1997 | Rockseisen |
| 5,675,625 A | 10/1997 | Rockseisen |
| 5,689,545 A | 11/1997 | Hopkins |
| 5,734,694 A | 3/1998 | Khutoryansky et al. |
| 5,745,545 A | 4/1998 | Hughes |
| 5,835,562 A | 11/1998 | Ramsdell et al. |
| 5,878,072 A | 3/1999 | Greisz |

(Continued)

OTHER PUBLICATIONS

International Search Report and Written Opinion dated Jan. 19, 2011.

(Continued)

*Primary Examiner* — Gregory J Toatley
*Assistant Examiner* — Juan D Valentin
(74) *Attorney, Agent, or Firm* — Andrus, Sceales, Starke & Sawall, LLP (57) ABSTRACT

An alignment device includes an incoherent light source, a first convex lens, a mirror rod, and a second convex lens. The incoherent light source emits incoherent light that is received by the first convex lens that produces a low divergence light beam. The low divergence light beam is directed to the mirror rod that reflects the light beam to the second convex lens that focuses the light beam to a convergent light beam.

23 Claims, 5 Drawing Sheets

U.S. PATENT DOCUMENTS

| | | | |
|---|---|---|---|
| 5,883,746 A | 3/1999 | Zelenka | |
| 5,912,775 A | 6/1999 | Glockler | |
| 6,084,717 A | 7/2000 | Wood et al. | |
| 6,269,143 B1 | 7/2001 | Tachibana | |
| 6,271,514 B1 | 8/2001 | Thomas et al. | |
| 6,473,489 B2 | 10/2002 | Bani-Hashemi et al. | |
| 6,600,605 B1 | 7/2003 | Anikitchev | |
| 6,917,666 B2 | 7/2005 | Wollenweber | |
| 6,935,779 B2 | 8/2005 | Zhang et al. | |
| 7,147,370 B2 | 12/2006 | Xiaodong et al. | |
| 7,147,371 B2 | 12/2006 | Hecker | |
| 7,166,852 B2 | 1/2007 | Saracen et al. | |
| 7,440,192 B2 | 10/2008 | Morrissey et al. | |
| 7,595,881 B2 * | 9/2009 | Leonard et al. | 356/436 |
| 7,603,163 B2 | 10/2009 | McNeirney et al. | |
| 7,632,015 B2 | 12/2009 | Stayman et al. | |
| 7,789,561 B2 | 9/2010 | Wu et al. | |
| 7,798,709 B2 | 9/2010 | Haras et al. | |
| 7,898,665 B2 * | 3/2011 | Brukilacchio et al. | 356/417 |
| 7,928,410 B2 | 4/2011 | Ose et al. | |
| 7,934,869 B2 | 5/2011 | Ivanov et al. | |
| 2008/0013088 A1 | 1/2008 | Hessert et al. | |
| 2008/0043902 A1 | 2/2008 | Viswanathan | |
| 2009/0252290 A1 | 10/2009 | Plut et al. | |
| 2010/0246777 A1 | 9/2010 | Thompson et al. | |

OTHER PUBLICATIONS

Angelopoulou, Elli, The Reflectance Spectrum of Human Skin, University of Pennsylvania Department of Computer and Information Science Technical Report No. MS-CIS-99-29; 1999; pp. 1-14.

European Search Report dated Oct. 14, 2010.

* cited by examiner

VARIABLE COLOR INCOHERENT ALIGNMENT LINE AND CROSS-HAIR GENERATOR

CROSS REFERENCE TO RELATED APPLICATION

This application relates to and claims priority from U.S. Provisional Application Ser. No. 61/223,212, filed Jul. 6, 2009, which is incorporated by reference herein in its entirety.

FIELD OF THE DISCLOSURE

The present application is directed toward a device for generating a variable color beam from an incoherent light source. More specifically, the present disclosure is related to the generation of an alignment line or cross-hair from an LED, multiple LEDs or other incoherent light source, for use in the medical field for alignment of patients with imaging and/or treatment devices and the construction and security fields for alignment beams or planes.

BACKGROUND

In the medical industry, and other such diverse industries as construction and military applications, a coherent light source such as a laser is often used for alignment and/or targeting applications.

Laser light sources are often used as light beam generators in these applications in order to create light beams of sufficient brightness, narrowness, and depth of field. However, many generators of coherent light such as gas lasers are often larger and more expensive than incoherent light sources such as incandescent light bulbs. Furthermore, gas laser light sources require more power at typically higher voltages. These limitations spurred the relatively recent shift from gas lasers to diode lasers in the patient alignment field.

While gas lasers and diode lasers are available in a variety of visible light wavelengths, which are perceived by a user as a variety of colors, laser sources are dedicated to the generation of a single light wavelength. This is limiting in various targeting or alignment applications. The person or object at which the light beam is directed may have differing light reflectivity or absorption characteristics. Therefore, particular wavelengths or colors of light may be perceived with more ease or more difficulty depending upon the subject or target at which the light beam is directed.

Often in alignment or targeting applications, a cross or cross-hair of light beams is preferred to a point or line of light as a cross-hair provides an indication of alignment in two planes. When a cross-hair is desired, this may require the use of two coherent light source generators. Alternatively, a complex beam-splitting optical arrangement is required to direct the light along two optical paths, only to be realigned to form the cross-hair. These implementations only further contribute to the size and expense of the alignment or targeting device.

BRIEF DISCLOSURE

The present disclosure is related to an alternative light beam generator using an incoherent light source. An embodiment of the light beam generator disclosed herein includes an incoherent light source and a convex cylindrical lens. The convex cylindrical lens projects the light from the incoherent light source into an alignment line.

In an embodiment disclosed herein, the light beam generator may further include a prism positioned in the light beam after it passes through the cylindrical lens. The prism may be positioned and controlled such as to split the light beam and rotate a portion of the beam with respect to the other portion to produce a cross-hair.

In another embodiment of the light beam generator, one incoherent light source provides light to a horizontally oriented cylindrical lens and another incoherent light source provides light to a vertically oriented cylindrical lens for forming respective horizontal and vertical light beams. The beams may be directed through the use of one or more mirrors in an orientation such as to form a cross-hair on the subject.

In a still further embodiment of the disclosed light beam generator, the incoherent light source comprises an array with a plurality of incoherent light sources of varying colors. The light sources of the array may be controlled as a group or individually such as to control the color of the light beam produced by the generator.

DETAILED DISCLOSURE

Figure 1:
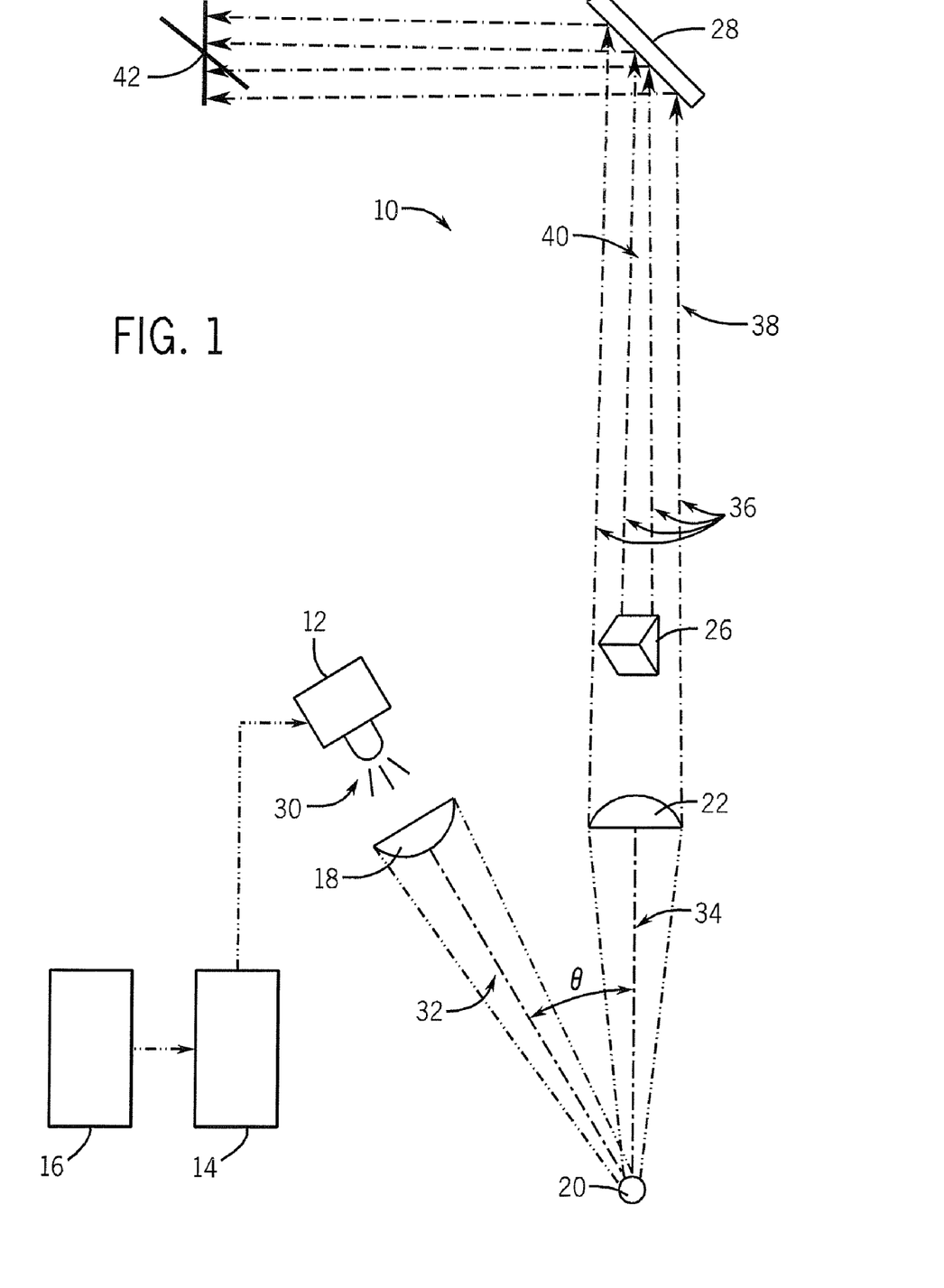
FIG. 1 is a system diagram depicting an embodiment of the cross-hair generator.

FIG. 1 is a schematic diagram of an embodiment of the light beam generator disclosed herein. The light beam generator 10 includes an incoherent light source 12. The incoherent light source 12 may include one or more sources of incoherent light which may include either incandescent, fiber optic, or LED incoherent light sources. If there are a plurality of incoherent light sources, the individual light sources are arranged in the incoherent light source 12 such as to form an array of light sources which may be a linear array. Each of the plurality of light sources may be controlled individually, or the light sources may be controlled as a group in order to further manipulate the intensity of the incoherent light produced by the light source 12.

To facilitate such control of the activation or intensity and wavelength of the resultant light source 12, the light source 12 is connected to control circuitry 14 which in turn is connected to power supply 16. The control circuitry 14 may include a combination of hardware and software controlled implementations to perform the control functions. In one embodiment, a processor is connected to a computer readable medium, storing computer readable code, or firmware that upon execution by the processor operates hardware of the control circuitry 14 to control the power delivered to the light source 12 and the activation of individual elements of the light source 12. The control circuitry 14 controls the light source 12 such as to selectively activate or deactivate individual light sources within the light source 12. In an additional embodiment, the control circuitry 14 operates the light source 12 with a pulse-width modulated (PWM) direct current (DC), such that the duty cycle of the current that is driving the light source 12 may be modified to control the intensities of specific light sources within the light source 12.

In the embodiment, the light source 12 is capable of providing incoherent light in a variety of color hues and wavelengths. This may be achieved through the use of a single light source such as a multi-color [e.g. Red-Green-Blue (RGB) or Red-Green-Blue-Amber (RGBA)], or a white LED. Alternatively, the light source 12 may be comprised of a linear array of individual colored light sources. The control circuitry 14 may be operated to control the individual light sources of the array of the light source 12 such as to activate one or more of the colored light sources to achieve the desired light color and intensity in the alignment cross-hair 42. If one or more white LEDs are used, the intensity of the white light may be controlled by control circuitry 14, while the light color is controlled through the use of a transparent color filter/wheel (not depicted).

The light source 12 generally produces widely divergent beams 30 of incoherent light. These beams 30 are directed through a convex cylindrical lens 18. The cylindrical lens collimates the incoherent light from the light source 12 such as to create a beam 32 of low divergence. The cylindrical lens 18 may be selected from various sizes and lengths such as to adequately match the size of the light source 12 and the dispersion of the light from light source 12. This allows for the cylindrical lens 18 to accept and collimate as much light as possible from the light source 12. The cylindrical lens 18 may be a plano-convex cylindrical lens or a double-convex cylindrical lens. While not intended to be limiting, the cylindrical lens 18 is preferably a full cylinder lens. If the light source 12 is an array comprising differently colored light sources, the cylindrical lens 18 helps to combine the divergent beams 30 from each of the light sources into a beam 32 of substantially even color.

The beam 32 from the cylindrical lens 18 is directed towards a cylindrical mirror rod 20. The mirror rod 20 is a convex cylindrical specular reflecting rod. As the beam 32 reflects off of the cylindrical mirror rod 20, the beam 34 diverges sharply and de-magnifies the image of light source 12.

Cylindrical lens 18 is positioned such as to form an angle θ between the beam 32 and the beam 34 reflected off the mirror rod 20. The control of the angle θ between the beam 32 and the beam 34 affects the resulting properties of the reflected beam 34. Preferably, the angle θ is an acute angle. The more acute the angle θ, the greater intensity of the beam 32 is reflected in beam 34. Widening the angle θ results in decreased intensity of the beam of light 34 and a greater demagnification effect, resulting in a thinner alignment line.

Beam 34 reflects off the cylindrical mirror rod 20 and is directed toward a convex cylindrical lens 22. The cylindrical lens 22 may be a plano-convex cylindrical lens or a double-convex cylindrical lens. The cylindrical lens 22 focuses the divergent beam 34 reflected off of the cylindrical mirror rod 20 and shapes the light into a slowly converging beam 36 of light. The slowly converging beam 36 of light from the cylindrical lens 22 is directed toward a prism 26. Half of the light from the cylindrical lenses 22 passes around the prism 26 forming a first plane in an original orientation. The other half of the light that passes through the prism 26 is rotated, forming a second plane 40 of light in a rotated orientation. Thus, the prism splits the beam 36 of light from the cylindrical lens 22 to form two intersecting planes of light.

In order to form the two equal lengths, intersecting planes of light, the prism 26 must be bathed in light such that an equal intensity of light is directed through the prism 26 as well as around the prism 26. In an embodiment, the cylindrical lens 22 may include one or more opaque coatings (not depicted) over portions of the cylindrical lens 22 such as to shape the beam of light emanating from the cylindrical lens 22, and to prevent undesired light refraction. However, it should be noted that closing down the aperture of lens 22 into too narrow of a slit such that the light intensity through the prism 26 and around the prism 26 is unbalanced, will substantially shorten the length of one line of the crosshair with respect to the other.

The prism 26, that in one embodiment is a right-angle or dove prism, is placed in the path of the beam 36 of light emanating from the cylindrical lens 22. The prism 26 is positioned such that the 90° apex of the prism and its base (typically its long axis) are centered on the optical axis with one 45° side facing upstream and the other 45° side facing downstream. When positioned in this manner, rotating the right angle dove prism 26 around the optical axis by 45° causes the portion of the beam of light that strikes the prism 26 to rotate about the optical axis by 90°. Thus, the plane of light emanated from the cylindrical lens 22 is split into two portions: a plane of light 38 that passes around the prism 26 remains in the original orientation of the beam, while a plane of light 40 that passes through the prism 26 is rotated 90° such that it is perpendicular to its original planar orientation. Thus, the single beam of light is split into two perpendicular, intersecting planes of light.

In an embodiment, the prism 26 is held in place within the beam of light from the cylindrical lens 22 through the use of a circular mount (not depicted), or other optical mounting system, that surrounds the prism 26. The circular mount may hold the prism 26 in place with a combination of points of contact between the circular mount and the prism 26. The points of contact may be positioned such as to not significantly interfere with the beam of light from the cylindrical lens 22. Screw adjustments on the circular mount may be used to rotate and adjust the prism 26 within the beam, such as to properly align the prism 26 at a 45° angle around the optical axis of the light beam.

The intersecting planes of light 38 and 40 from the prism 26 are then directed to a steering mirror 28. In an embodiment, the steering mirror 28 is a first-surface plane mirror. The steering mirror 28 is controlled or otherwise adjustable such as to direct and position the cross-hair generated by the system 10 at the targeted subject.

It should be noted that while the prism 26 and the steering mirror 28 are described as adjustable, this adjustment may be achieved through manual, mechanical, or electrical and software control. In these embodiments, a processor (not depicted) may be connected to electrical and/or mechanical controls to operate the adjustment of the prism 26 or the steering mirror 28 through the execution of software code.

As previously mentioned, embodiments as disclosed herein may be used in the medical field for purposes of positioning or aligning patients on medical imaging and/or treatment devices. In a more specific implementation, an embodiment of the device as disclosed herein may be used as a patient positioning aid for radiation oncology procedures. The perpendicular planes of light generated by this apparatus are arranged in such a fashion as to be directed onto the patient to indicate the positioning of the plane wherein the oncological target resides within the patient. When three separately generated planes are used, their intersection locates the center of the target inside the patient. This alignment may be initially setup during the computed tomography (CT) simulation phase of the treatment process. In this phase, a specially modified CT scanner is used to locate the target within the patient. Alignment planes generated by the disclosed apparatus indicate positional alignment between the CT scanner and the patient. The patient may then be marked to indicate where the alignment planes locate on the properly aligned patient.

After this marking is performed on the patient, one or more additional cross-hair generators, as disclosed herein, may be arranged in the radiation treatment room and positioned in such a manner such that the intersection of the light planes created by the beam generators coincides with the isocenter of the radiation treatment beam. This way, when the patient is placed on the linear accelerator table, the patient can be properly positioned with respect to the treatment beam by aligning the light from the presently disclosed beam generator with the marks on the patient which were previously placed during the CT simulation.

While one specific embodiment regarding an oncological application has been disclosed herein, other such applications requiring positioning and/or alignment of patients on a medical device may find utility with an embodiment of the presently disclosed device. Non-limiting examples of such applications may include CT scanners, conventional (digital and analog) x-ray, interventional radiology, bone mineral analysis, and magnetic resonance imaging (MRI). In all of these radiological applications, presently disclosed embodiments could be used to position the patient in preparation for imaging.

Figure 2:
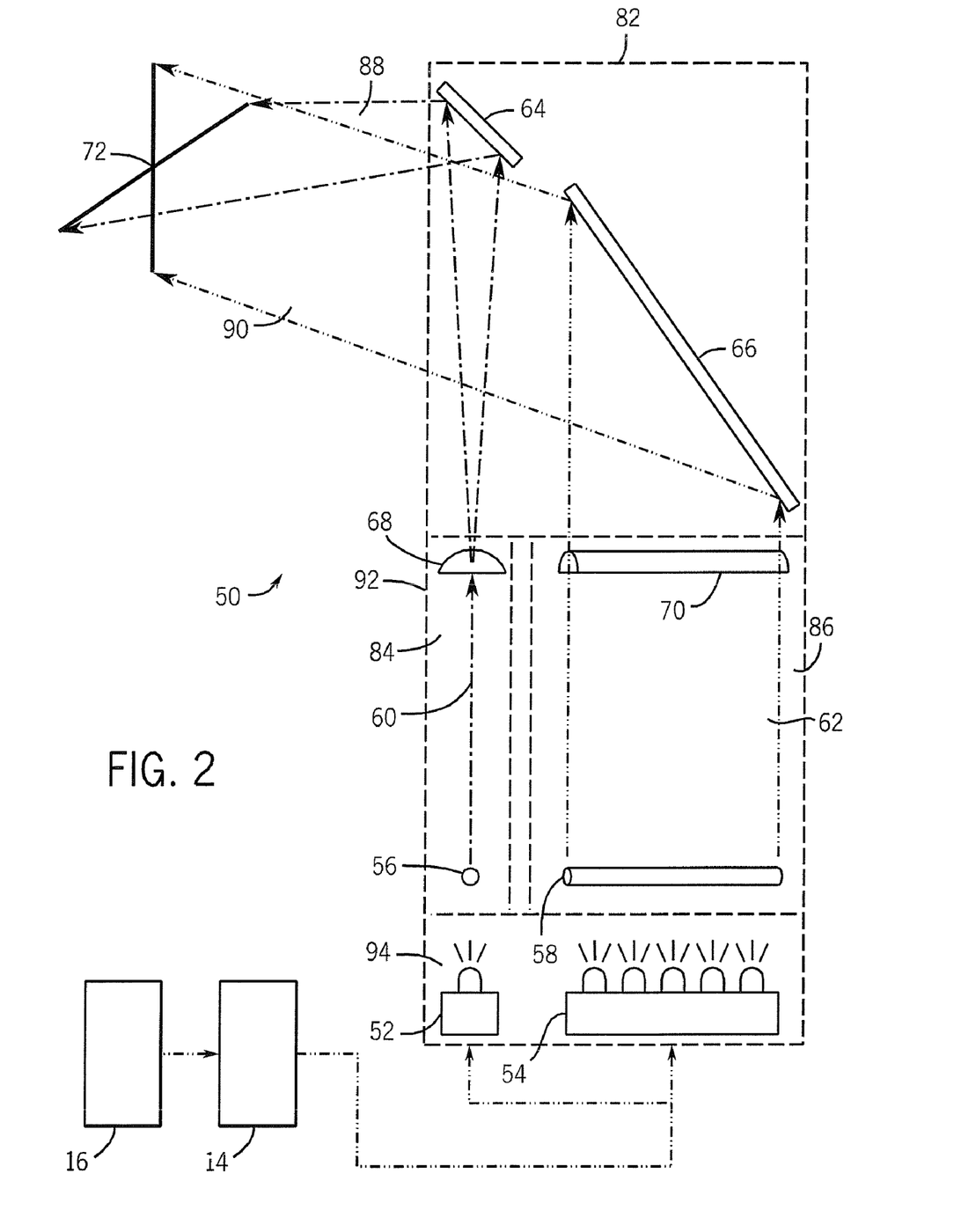
FIG. 2 depicts a further embodiment of the cross-hair generator.

FIG. 2 depicts an additional embodiment of the cross-hair generator 50. The cross-hair generator 50 includes two optical systems that are coordinated to produce the generated cross-hair 72. A first system which includes first light source 52, first cylindrical lens 56, second cylindrical lens 68 and first steering mirror 64. A second system includes second light source 54, third cylindrical lens 58, fourth cylindrical lens 70 and second steering mirror 66.

To facilitate such control of the activation or intensity of the light sources 52 and 54, the light sources 52 and 54 are connected to control circuitry 14, which in turn is connected to power supply 16. The control circuitry 14 may include a combination of hardware and software controlled implementations to perform the control functions. In one embodiment, a processor is connected to a computer readable medium, storing computer readable code, or firmware that upon execution by the processor operates hardware of the control circuitry 14 to control the power delivered to the light sources 52 and 54 and the activation of individual elements of the light sources 52 and 54. The control circuitry 14 controls the light sources 52 and 54 such as to selectively activate or deactivate individual light sources within the light sources 52 and 54. In an additional embodiment, the control circuitry 14 operates the light sources 52 and 54 with a pulse-width modulated (PWM) direct current (DC), such that the duty cycle of the current that is driving the light sources 52 and 54 may be modified to control the intensities of specific light sources within the light sources 52 and 54.

In the embodiment 50, the light sources 52 and 54 are capable of providing incoherent light in a variety of color hues and wavelengths. This may be achieved through the use of a single light source such as a multi-color LED (RGB, RGBA) or a white LED filtered to obtain individual color output. Alternatively, the light sources 52 and 54 may be comprised of an array of individual colored light sources. The control circuitry 14 may be operated to control the individual light sources of the array of the light sources 52 and 54 such as to activate one or more of the colored light sources to achieve the desired light color and intensity in the alignment cross-hair 72. If one or more white LEDs are used, the intensity of the white light may be controlled by control circuitry 14, while the light color is controlled through the use of one or more transparent color filters (not depicted). In one embodiment, the one or more transparent color filters are arranged in a rotatable wheel.

The cross-hair generator 50, includes a structure 92 within which components of the cross-hair generator 50 are disposed. The structure 92 includes a series of conduits and enclosures that help to facilitate the optical functions of the elements of the cross-hair generator 50. Embodiments of the structure 92 include a first light-tight enclosure 94. The first light source 52 and the second light source 54 are disposed within the first light-tight enclosure 94. The interior of the first light-tight enclosure 94 is flat black in color to eliminate stray light.

A first light-tight conduit 84 and a second light-tight conduit 86 extend from the first light-tight enclosure 94 to a second light-tight enclosure 82. The light-tight conduits 84 and 86 may be, but need not be, cylindrical in shape. The light-tight conduits 84 and 86 may be made of a light-absorptive material such as to cut down on stray light and prevent contamination of the first beam 60 and the second beam 62 which are projected within the respective first light-tight conduit 84 and second light-tight conduit 86. First cylindrical lens 56 and third cylindrical lens 58 are respectively located in the first light-tight conduit 84 and the second light-tight conduit 86. The second cylindrical lens 68 and fourth cylindrical lens 70 are located at an opposite end of the first and second light-tight conduits 84 and 86.

The second light-tight enclosure 82, which may be a dark or black light-absorptive color such as to further reduce light contamination of the light beams, houses the steering mirrors 64 and 66. The steering mirrors 64 and 66 direct the beams 60 and 62 out of the second light-tight enclosure 82.

The first light source 52 and the second light source 54 are variable color incoherent light sources. These variable colored, incoherent light sources may be implemented through the use of one or more multi-color light sources, such as RBG, RGBA, or white LEDs with color filters, or may be implemented as a linear array of single color incoherent light sources, such as individually colored LEDs or fiber optic lights. The individually colored light sources of the first and second light sources 52 and 54 may be controlled such as to activate one or more of the individual light sources in a combination to provide a variety of color and hues of incoherent light.

The incoherent light from light sources 52 and 54 is directed toward the first cylindrical lens 56 and third cylindrical lens 58, respectively. The first and third cylindrical lenses 56 and 58 may be convex cylindrical lenses, which de-magnify the incoherent light from the light sources 52 and 54 to form a first beam of light 60 and a second beam of light 62.

The first beam of light 60 and the second beam of light 62 are directed through the first light-tight conduit 84 and the second light-tight conduit 86, respectively, toward first cylindrical lens 68 and second cylindrical 70, respectively. Cylindrical lenses 68 and 70 are adjustable along their optical axes to allow fine focusing of the projected alignment lines on the alignment subject. Beams 60 and 62 then strike steering mirrors 64 and 66, respectively. Steering mirrors 64 and 66 are first-surface plane mirrors. Steering mirror 64 reflects the first beam 60 out of the structure 92 as a first plane of light 88. Steering mirror 66 reflects the second beam 62 out of the structure 92 as second plane of light 90. First plane 88 and second plane 90 form an alignment cross-hair 72 on a subject (not depicted) when projected on the subject.

Adjusting the angles of the orientation of the steering mirrors 64 and 66 modifies the first plane of light 88 and the second plane of light 90 out of the structure 92. The steering mirrors 64 and 66 may be adjusted to coincide with the horizontal and vertical planes of the treatment machine geometry, or to fulfill other alignment purposes.

As noted previously with respect to the steering mirror in FIG. 1, the steering mirrors 64 and 66 may be adjusted manually, or may be configured for mechanical, electromechanical, or software implemented control of the alignment of the first plane 88 and second plane 90 to form the cross-hair 72.

The separate optical systems of embodiment 50 allow for the separate generation and control of the first plane 88 and the second plane 90 making up the cross-hair 72. The control and positioning of the cross-hair 72 is achieved through control of the position and angle of the steering mirrors 64 and 66 such that the cross-hair 72 may be adjusted or recalibrated to ensure that the projected cross-hair 72 is square and located in the proper alignment with the positioned patient.

Figure 3:
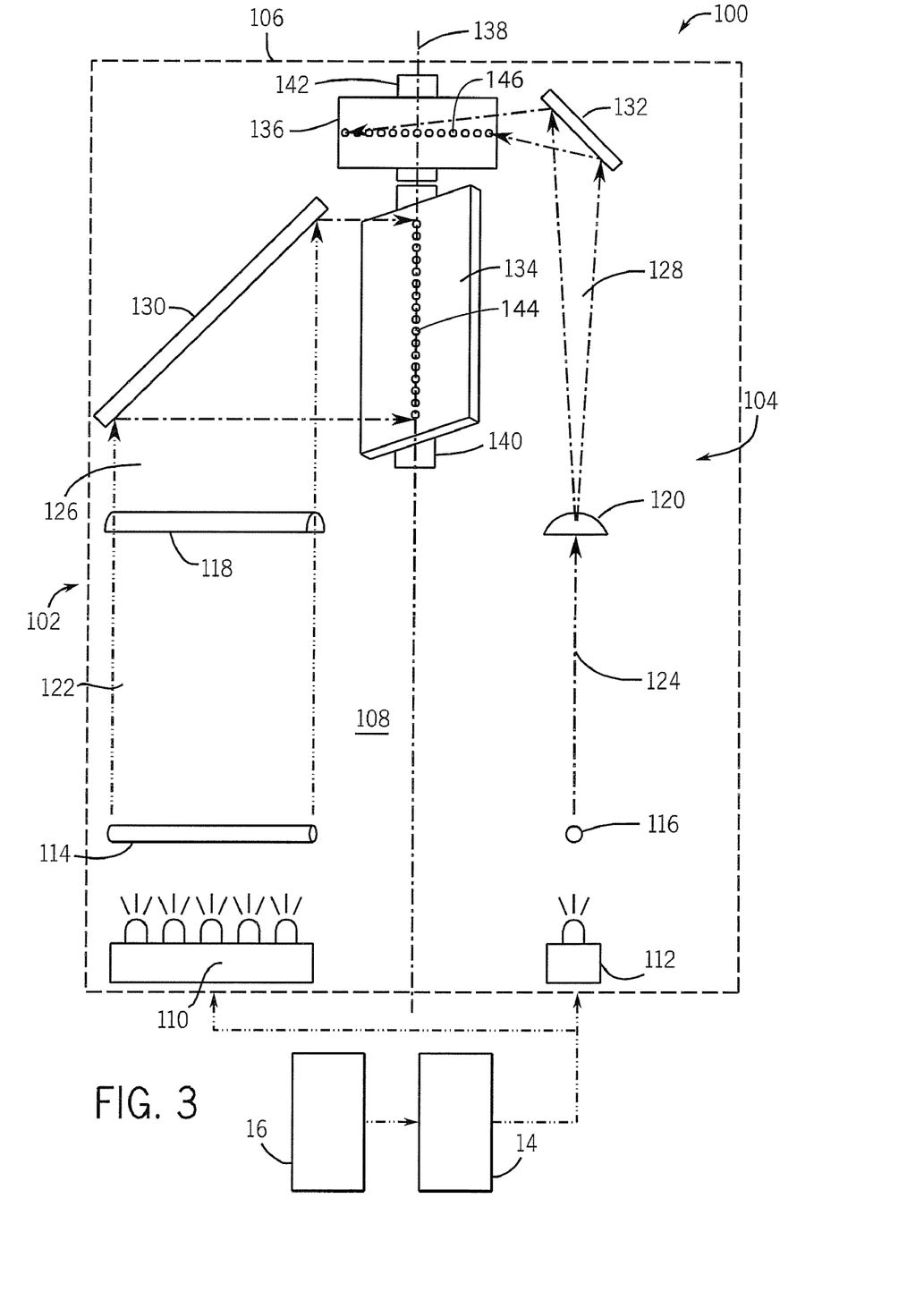
FIG. 3 depicts an embodiment of the cross-hair generator with a low depth profile.

FIG. 3 depicts a further embodiment of the cross-hair generator 100. Similar to the cross-hair generator 50 depicted in FIG. 2, the cross-hair generator 100 includes two alignment line generation systems. A first system 102 comprises a first light source 110, first de-magnifying lens 114, first projection lens 118, first steering mirror 130, and first centerline mirror 134. A second system 104 comprises a second light source 112, second de-magnifying lens 116, second projection lens 120, second steering mirror 132, and second centerline mirror 136.

The first system 102 and the second system 104 are both mounted to a base plate surface 108 and housed within a structure 106 which retains the first system 102 and the second system 104 in isolation from light contamination. In one merely descriptive use, the structure 106 may be mounted on a wall (not depicted) in a generally vertical orientation. While the cross-hair generator 100 may be used in alternative orientations, the following description will relate to this exemplary orientation. When the structure 106 is mounted in a generally vertical orientation on a wall, then the first system 102 generates a vertical alignment line and the system 104 generates a horizontal alignment line.

The following description will herein focus on the first system 102, and it is to be recognized that this description also generally applies to the second system 104, except where noted.

The first system 102, which generates a vertical alignment line 144, includes a first light source 110. The first light source 110 may be similar to the light sources described herein with respect to the other embodiments and may include an array of individual incoherent light sources. The first light source 110 is arranged generally parallel to the base plate surface 108. A first cylindrical de-magnifying lens 114 is aligned with the first light source 110. Similar to the first light source 110, the first de-magnifying lens 114 is aligned parallel to the base plate surface 108. The first de-magnifying lens 114 may be a cylindrical lens with a merely exemplary diameter of 1 mm. The first de-magnifying lens 114 receives the incoherent light from the first light source 110 and de-magnifies the light in the direction of the first projection lens 118. In embodiments of the cross-hair generator 100 that use a first light source 110 with a variety of colors of incoherent light sources, the de-magnification of the incoherent light by first de-magnifying lens 114 helps to create a light beam 122 of an even color and intensity.

The light beam 122 extends generally parallel to the base plate surface 108 towards the first projection lens 118. The first projection lens 118 is a cylindrical projection lens, which may be a convex or a plano-convex projection lens. In an exemplary embodiment, the first projection lens 118 has a merely exemplary diameter of 150 mm. It is understood that other diameter lens may be used in alternative embodiments.

A non-power axis of the first projection lens 118 is aligned parallel with the base plate surface 108. The first projection lens 118 receives the de-magnified light beam 122 and focuses the de-magnified light beam 122 into a focused light beam 126 that extends in a direction parallel to the base plate surface 108.

The first steering mirror 130 receives the focused light beam 126 from the first projection lens 118 and reflects the focused light beam 126 in the direction of the center line 138 of the structure 106. The first steering mirror 130 is a first surface minor that is aligned perpendicular to the base plate surface 108 and is angled at a 45° angle with the center line 138.

The first center line mirror 134 is a rectangular mirror that is arranged with its long axis oriented parallel with the central line 138. The first center line mirror 134 is a first-surface mirror that extends away from the base plate surface 108 at an adjustable angle. In the exemplary embodiment, the first center line mirror 134 angles away from the base plate surface 108 at a 45° angle. The first center line mirror 134 is supported on the center line 138 by its connection to a movable mirror mount 140. The mirror mount 140 may be manually, mechanically, or electro-mechanically moved to adjust the angle of the first center line mirror 134 with the base plate surface 108 in order to adjust the horizontal adjustment and/or vertical adjustment of the vertical alignment line 144.

The second system 104 generates the horizontal alignment line. The second system 104 operates in a manner similar as described above with respect to the first system 102. The difference in the arrangement of the structure of the second system 104 is that the structures are aligned perpendicular to the base plate surface 108, rather than parallel to the base plate surface 108. Specifically, the second light source 112 and the second de-magnifying lens 116 are arranged perpendicular to the base plate surface 108. The non-power axis of the second projection lens 120 is also oriented perpendicular to the base plate surface 108. A long axis of the second steering mirror 132 is oriented perpendicular to the base plate surface 108. The second steering mirror 132 is further angled at a 45° angle towards the center line 138 such as to direct the light beam 128 from the second projection lens 120 toward the center line 138 of the structure 106.

The second center line mirror 136 is aligned with its long axis perpendicular to the center line 138. The second centerline mirror 136 adjustably angles away from the base plate surface 108. The specific angle between the second center line mirror 136 and the base plate surface 108 is controlled by an adjustable mirror mount 142. The movable mirror mount 142 may be manually, mechanically, or electro-mechanically operated to adjust the angular position of the second center line mirror 136 with respect to the base plate surface 108. The light beam 128 reflected off of the second steering mirror 132 is further reflected off of the second center line mirror 136 out of the structure 106 as the horizontal alignment line. Rotation of the second center line mirror 136 about the mirror mount 142 permits horizontal adjustment and/or vertical adjustment of the horizontal alignment line 146.

The cross-hair generator 100 depicted in FIG. 3 arranges the first system 102 and the second system 104 in a side-by-side relationship within the structure 106, rather than a front-to-back relationship between the first system and the second system of the cross-hair generator 50 depicted in FIG. 2. This minimizes the depth profile of the cross-hair generator 100 and therefore minimizes protrusion of the cross-hair generator 100 from a wall (not depicted) to which it is exemplarily mounted.

The arrangement of the center line mirrors 134 and 136 on mirror mounts 140 and 142 on the center line 138 allows the horizontal alignment line and the vertical alignment line to be individually adjusted to account for skew. The cross-hair generator 100 can therefore be calibrated to create a cross-hair with exact perpendicularity between the horizontal alignment line and the vertical alignment line.

Figure 4:
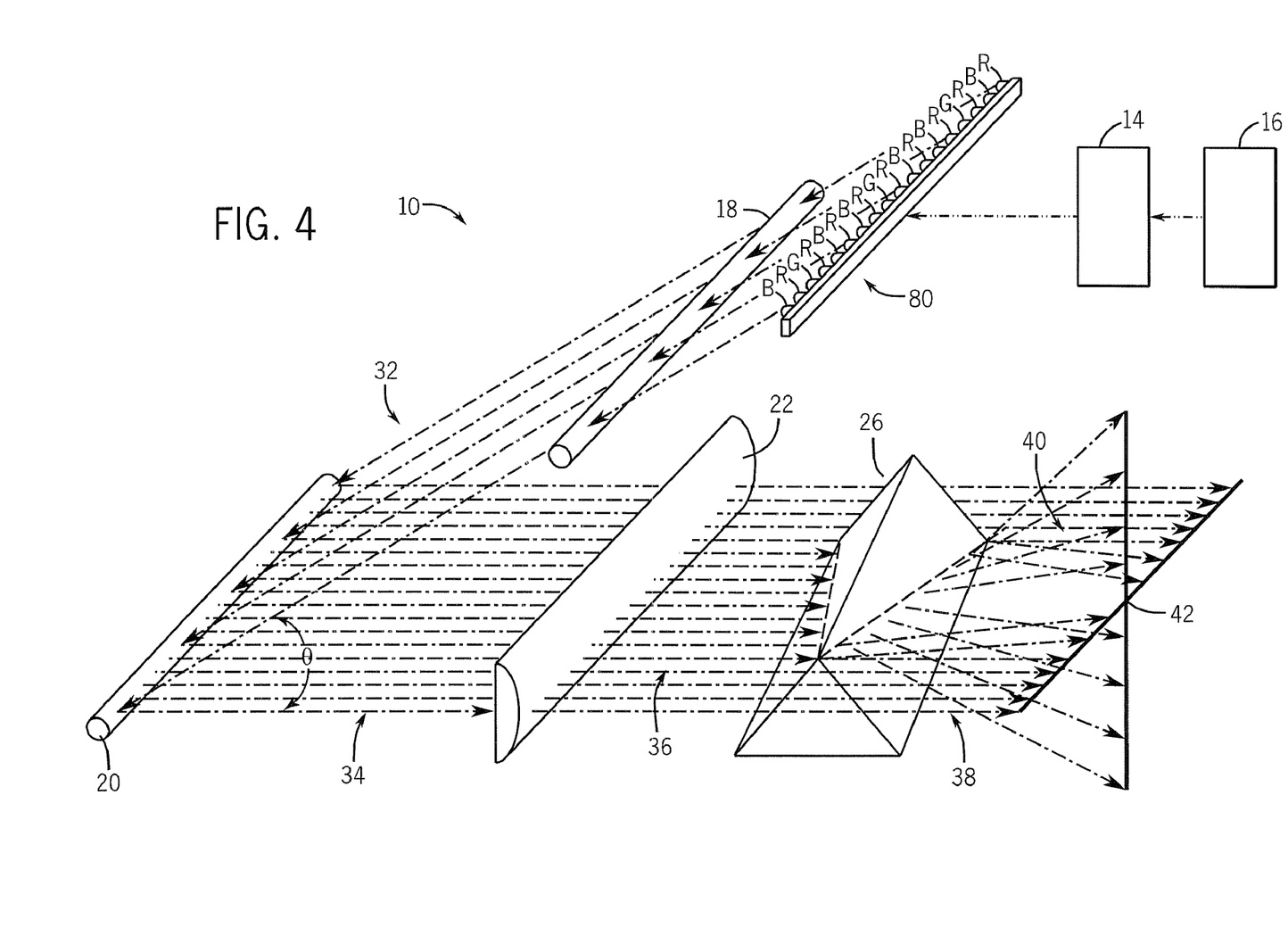
FIG. 4 depicts an embodiment of the cross-hair generator with a multi-colored incoherent linear light source.

FIG. 4 depicts another view of an embodiment similar to the embodiment depicted in FIG. 1 wherein like components are numbered the same. One of the differences of the embodiment of FIG. 4 is that the light source 80 is a linear array of individual light sources. However, many types of incoherent light sources may be used in such an array. Other embodiments may include multi-color (RGB, RGBA) elements, or the like. More specifically, this embodiment includes an array of colored LED light sources. Depicted in this embodiment is a 1×18 array of colored LEDs. It should noted that while a 1×18 light array is depicted, other formations of light source arrays may be used.

As indicated in FIG. 4, the light source 80 includes a particular order or arrangement of colored LEDs. In an exemplary embodiment, the particular order used is as follows: blue, red, green, red, blue, red, blue, red, green, red, blue, red, blue, red, green, red, blue, red. This particular arrangement of LEDs is intended to be non-limiting on the present disclosure. It is to be noted that this particular arrangement was chosen due to the light intensities of the various colored LEDs used in an exemplary embodiment. More specifically, the particular disclosed arrangement was selected to produce even amounts of light intensity from the red, blue, and green LED light sources. In other words, since the particular green LEDs used in this embodiment produce a more highly visible green light component than the visibility of red light produced by the red LEDs, the presently disclosed embodiment utilizes three red LEDs for every green LED in the light source 80.

While balanced light intensities from the different colored sources in the light source 80 simplify the operation and control of the light source 80, they are not necessary in all embodiments. Balancing of the light intensities may be achieved through power control to the different colored light sources. For example, this same balancing may be achieved by operating the red LEDs at a higher duty cycle than that of the green LEDs. When all of the red, blue, and green LEDs are operated at a balanced intensity, a cross-hair 42 of white light is achieved. Alternatively, the light source 80 may be operated in an unbalanced intensity state.

To facilitate such control of the activation or intensity of the light source 80, the light source 80 is connected to control circuitry 14, which in turn is connected to power supply 16. The control circuitry 14 may include a combination of hardware and software controlled implementations to perform the control functions. In one embodiment, a processor is connected to a computer readable medium, storing computer readable code, or firmware that upon execution by the processor operates hardware of the control circuitry 14 to control the power delivered to the light source 80 and the activation of individual elements of the light source 80. The control circuitry 14 controls the light source 80 such as to selectively activate or deactivate individual light sources within the light source 80. In an additional embodiment, the control circuitry 14 operates the light source 80 with a pulse-width modulated (PWM) direct current (DC), such that the duty cycle of the current that is driving the light source 80 may be modified to control the intensities of specific light sources within the light source 80.

In the embodiment, the light source 80 is capable of providing incoherent light in a variety of color hues and wavelengths. This may be achieved through the use of a single light source such as a multi-color (RGB, RGBA), or white (filtered) LED. Alternatively, the light source 80 may be comprised of an array of individual colored light sources. The control circuitry 14 may be operated to control the individual light sources of the array of the light source 80 such as to activate one or more of the colored light sources to achieve the desired light color and intensity in the alignment cross-hair 42. If one or more white LEDs are used, the intensity of the white light may be controlled by control circuitry 14, while the light color is controlled through the use of a transparent color filter/wheel (not depicted).

Referring to the rest of the embodiment depicted in FIG. 4, it is to be noted that no steering mirror is included in this embodiment; however, it is possible for such a mirror to be included for re-directing the cross-hair 42 to adjust for alignment on the target object.

As mentioned before, the smaller the θ angle between beam of light 32 and beam of light 34, the greater intensity of light beam 34, while a greater angle θ increases the demagnification of the individual LED light sources from light source 80.

Additionally, FIG. 4 provides an additional view of the beams of light as they are manipulated to form the cross-hair 42. More specifically, the prism 26 can be seen more clearly to be disposed within the beam of light 36, such that a first portion 38 of the beam 36 passes around the prism 26, while another portion of the beam 36 is refracted through the prism 26 to a vertical orientation such as to form a second beam of light 40. In an embodiment, the prism 26 is bathed in light, such that the entire prism 26 receives light from beam 36. The balancing of the intensities of light projected into the prism 26 and around the prism 26 facilitates the creation of a balanced cross-hair in length and intensity.

In one embodiment, the prism 26 is a right-angle dove prism. The dove prism 26 may be positioned and controlled to manipulate the light refracted through the prism such as to rotate the plane of light by 90°, thus creating the second beam of light 40. In one embodiment, the dove prism may be rotated by 45° such as to achieve the desired second beam of light 40. However, it is to be noted that based upon the dimensions of the prism 26, the specific positioning of the prism 26 within the beam of light 36 may vary such as to accurately produce the desired second beam of light 40.

Referring back to the light source 80 of FIG. 4, a light source that is formed of a linear array of light sources, such as the presently disclosed light source 80 of FIG. 4, presents additional features and advantages that may be found in the embodiment.

Based upon technological convention and the trichromatism of human visual perception, the light source 80 includes individual blue, red, and green light sources. The additive property of these light sources allows for the creation of a cross-hair 42 of varying colors. In a most basic example, activation of only the red elements of the light source will produce a red cross-hair 42, activation of only the blue elements will produce a blue cross-hair 42, and activation of only the green elements will produce a green cross-hair 42. The activation of combinations of the individual colored elements allows for creating a cross-hair 42 of a variety of colors. As noted earlier, the individual color elements have been selected to balance the intensities of the available color light source elements in this embodiment. Therefore, when all of the colored light source elements are illuminated, each of the three colors of light are produced in equal intensities, thus producing a white light.

In embodiments such as that depicted in FIG. 4, the light source 80 is spaced apart from the cylindrical lens 18 such that the individual colors of the light emitted from each of the light elements is able to mix and is evenly projected onto the cylindrical lens 18. The cylindrical lens 18 further provides the function of concentrating the light as it is produced from the plurality of individual light elements of the light source 80 in order to further evenly mix the light beam 32.

As further disclosed above, each of the light elements of the light source 80 may be powered by a pulse width modulated direct current (DC) such that the duty cycle of each of the light elements may be adjusted, further controlling and increasing the variety of color hues produced by the light source 80.

The advantages of such an implementation may be further explained through some specific examples. The perception of a color is based upon two main considerations. First, the perceived color is based upon the technician's anatomic ability to perceive color. While most humans are trichromatic, having light receptive structures with peak sensitivity to low, medium, and high visible light wavelengths, some individuals suffer from various forms of color blindness, with reduced perception of various light wavelengths. Color blindness predominantly affects males, affecting approximately 5%-10% of the male population. In the predominant forms of color blindness, the individual's ability to perceive the colors red and green are impaired.

The second factor in determining perception of a color is the reflectance of the object which is being illuminated and perceived. More specifically, an object's color is based upon the amount of each wavelength of light that is reflected (alternatively which color wavelengths are absorbed) by the object. Thus, the perceived color of an object is based upon the received intensities of the wavelengths of light reflected off of the object.

These two considerations are important in medical patient alignment applications. First, based upon the skin tone of the patient, various colors reflect better off of various patient skin tones, while other colors are absorbed more readily by various skin tones.

Figure 5:
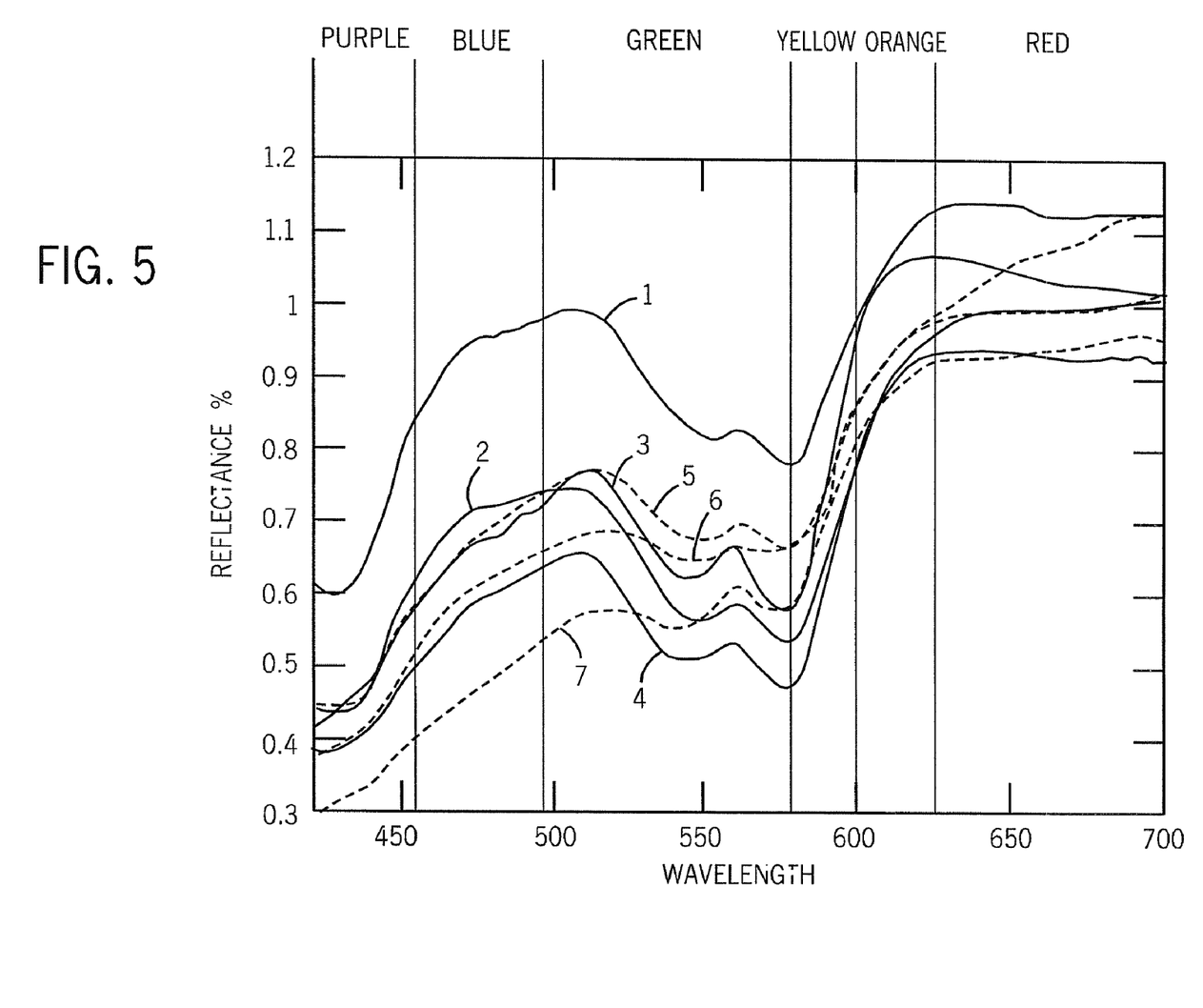
FIG. 5 is a graph depicting the reflectance of different light wavelengths on human skin with differing melanin levels.

FIG. 5 is a graph showing varying percentages of reflectance of different light wavelengths based upon subject skin tone. Angelopoulou, Elli, "The Reflectance Spectrum of Human Skin," Technical Report No. MS-CIS-99-29, FIG. 5, University of Pennsylvania Dept. of Computer and Information Science (1999). Available at: http://repository.upenn.edu/cis_reports/584. The various lines represent the reflectance of various skin tones across the visible light spectrum. Lines 1-4 represent varying skin tones found in people of Caucasian descent. Lines 5 and 6 represent skin tones in people of Indian descent. Line 7 represents skin tones in people of African descent. This graph thus shows the differences in reflectance properties of various skin tones.

Therefore, it is desirable to be able to adjust the color of the alignment cross-hair to a color hue that maximizes the reflectance based upon the patient's skin tone.

The reflectance of a patient's skin for various wavelengths of light is generally determined by two considerations. First, the amount of the pigment melanin present in the epidermis layer of the patient's skin generally determines the overall reflectance of a person's skin. Additionally, the hemoglobin found in oxygenated blood in the derma layer of the patient's skin further has a characteristic impact on skin reflectance mainly in medium wavelength light (500-600 nm).

As can be seen in the graph at FIG. 5, under many conditions and patient skin tones, the red spectrum of visible light is the most reflective. However, outside of red light, the reflectance for other various colors of light is much more varied.

With respect to a user who suffers from color blindness, if red and green light is difficult for a user to perceive, then adjustment of the light across the spectrum is desirable in order to identify a color that maximizes the user's visual perception of the generated cross-hair.

Therefore, the present cross-hair generator allows for the adjustment of the color of the generated cross-hair to maximize the perception of the alignment cross-hair by the technician. This includes adjustments based upon the skin tone of the patient, as well as further adjustments if the technician exhibits one of the many forms of color blindness.

The reflectance of a specific subject's skin may be measured by shining individually colored lights on the subject simultaneously and side-by-side. A user may then select from the various colors, the color at which the user finds to be subjectively most visible. Additionally, a cast of judges representing various user groups delineated by various characteristics, including specifically age and gender, may be used to generically identify specific colors and wavelengths that are most readily visible to a user of that demographic category and the skin tone of the patient. Additionally, patients of various color, tone, and shade of skin may be used to further subjectively assess the preferred operating color under various conditions. The resulting subjective data may be stored in the form of a look-up table such that based upon the characteristics of the patient and the user, a suggested optimal color may be determined.

Alternatively, spectroradiometers and filter photometers could be implemented, separately or integrally with the cross-hair generator to quantify the subjective judgments referred to above. A similar procedure of testing changes patient skin tones and measures the reflective intensities of various colors of light. In embodiments using a special radiometer or filter photometer, a user may be able to test his or her color perception in order to establish personalized defaults or color settings to be used with patients of various skin tones.

Other applications of a multi-color alignment beam could be found in the construction industry, wherein a device such as a laser level may be modified as disclosed herein to produce a varying color of alignment beam in order to maximize perception based upon the user's perception abilities and the reflectance of the surface or object upon which the alignment beam is projected.

In another such application, in the security industry, the color of the alignment beam may be adjusted using features of a disclosed embodiment such as to either maximize or inhibit visual perception of an alignment beam or alignment plane in a various location, such as may be used for security purposes.

This written description uses examples to disclose various embodiments, including the best mode, and also to enable any person skilled in the art to make and use these embodiments. The patentable scope as defined by the claims may extend to include other examples not explicitly listed that occur to those skilled in the art. Such other examples are intended to be within the scope of the claims if they have structural elements that do not differ from the literal language of the claims, or if they include equivalent elements with insubstantial differences from the literal languages of the claims.

Various alternatives and embodiments are contemplated as being within the scope of the following claims, particularly pointing out and distinctly claiming the subject matter of the present disclosure.

We claim:

1. An alignment device for use in the alignment of a subject, the alignment device comprising:
   an incoherent light source, wherein the incoherent light source is a multi-color light source that emits incoherent light;
   a first convex cylindrical lens that receives the incoherent light and collimates the incoherent light to produce a low divergence light beam;
   a mirror rod, wherein the low divergence light beam is directed to and reflected off of the mirror rod, wherein the mirror rod demagnifies and diverges the low divergence light beam;
   a second convex cylindrical lens that receives the divergent and demagnified light beam from the mirror rod and focuses the divergent and demagnified light beam to a convergent light beam directed at the subject; and
   a controller coupled to the incoherent light source, the controller operating the incoherent light source to produce incoherent light of a selected wavelength.

2. The alignment device of claim 1 wherein the wavelength of the incoherent light emitted from the incoherent light source is adjusted to a wavelength of optimal reflectance from the subject.

3. The alignment device of claim 1 wherein the alignment of the first convex cylindrical lens, the mirror rod and the second convex cylindrical lens form an angle theta, and the angle theta is adjusted to control the demagnification of the convergent light beam directed at the subject.

4. The alignment device of claim 1 further comprising a prism disposed within the convergent light beam, the prism splitting the convergent light beam into first and second beam portions that form a cross-hair directed at the subject.

5. The alignment device of claim 4 wherein the prism is a right-angle or dove prism and the prism is rotated 45 degrees about its optical axis.

6. The alignment device of claim 4 further comprising a circular mount that retains the prism within the convergent light beam, the circular mount further being adjustable such as to position the prism within the convergent light beam.

7. The alignment device of claim 4 further comprising a steering mirror that reflects the cross-hair, the steering mirror being adjustable such as to direct the cross-hair at the subject.

8. An alignment device for use in the alignment of a subject, the alignment device comprising:
   an array of incoherent light sources, the array selectively producing a plurality of wavelengths of incoherent light;
   a first convex cylindrical lens that receives incoherent light from the array and collimates the incoherent light to produce a low divergence light beam;
   a mirror rod, wherein the low divergence light beam is directed to and reflected off of the mirror rod, wherein the mirror rod demagnifies and diverges the low divergence light beam; and
   a second convex cylindrical lens that receives the divergent and demagnified light beam from the mirror rod and focuses the divergent and demagnified light beam to a convergent light beam directed at the subject.

9. The alignment device of claim 8 wherein the incoherent light sources of the array are multi-colored light emitting diodes (LEDs).

10. The alignment device of claim 8 wherein the array comprises incoherent light sources of at least a first color and a second color.

11. The alignment device of claim 8 further comprising a controller coupled to the array, the controller operating the incoherent light sources of the array to produce the plurality of wavelengths of incoherent light.

12. The alignment device of claim 11 wherein the controller further operates the incoherent light sources of the array at varying intensities.

13. The alignment device of claim 11 further comprising a prism positioned within a path of the convergent light beam, the prism splitting the convergent light beam into first and second beam portions that form a cross-hair directed at the subject.

14. The alignment device of claim 13 further comprising a steering mirror that reflects the cross-hair, the steering mirror being adjustable such as to direct the cross-hair at the subject.

15. An alignment turret projecting an alignment beam on a subject, the alignment turret comprising:
   at least one incoherent light source that emits incoherent light of a selectively variable wavelength;
   a first optical system including a first cylindrical lens, a first steering mirror, and a second cylindrical lens, the first optical system receiving incoherent light from the at least one incoherent light source through the first cylindrical lens and projecting a convergent and demagnified first alignment beam at the subject;
   a second optical system including a third cylindrical lens, a second steering mirror, and a fourth cylindrical lens, the second optical system receiving incoherent light from the at least one incoherent light source through the third cylindrical lens and producing a convergent and demagnified second alignment beam at the subject and orthogonal to the first alignment beam.

16. The alignment turret of claim 15 further comprising of:
   a light-tight enclosure within which the first steering mirror and the second steering mirror are disposed and the second cylindrical lens and the fourth cylindrical lens are mounted to the outside of the light-tight enclosure such that the second cylindrical lens and the fourth cylindrical lens are orthogonal to one another;
   wherein the first steering mirror reflects a beam of light from the first cylindrical lens and directs the beam of light through the second cylindrical lens and the second steering mirror reflects a beam of light from the third cylindrical lens and directs the beam of light through the fourth cylindrical lens.

17. The alignment turret of claim 16, wherein the at least one incoherent light source is a first incoherent light source array associated with the first optical system and a second incoherent light source array associated with the second optical system.

18. The alignment turret of claim 17, further comprising:
   a first light-tight conduit associated with the first optical system, the first light-tight conduit extending from the first cylindrical lens to the light-tight enclosure; and
   a second light-tight conduit associated with the second optical system, the second light isolation conduit extending from the third cylindrical lens to the light-tight enclosure.

19. The alignment turret of claim 15 further comprising a central axis through the alignment turret, the alignment turret being rotatable about the central axis such as to project the first alignment beam and the second alignment beam on the subject.

20. The alignment structure of claim 15 wherein the first steering mirror directs its beam toward the center line of the structure instead of immediately out of the structure.

21. The alignment structure of claim 15 wherein the second steering mirror directs its beam toward the center line of the structure instead of immediately out of the structure.

22. The alignment structure of claim 20 wherein a first center line mirror located at the center line of the structure directs the line beam from the first steering mirror out of the structure and on the subject.

23. The alignment structure of claim 20 wherein a second center line mirror located at the center line of the structure directs the line beam from the second steering mirror out of the structure and on the subject.

* * * * *